US011562268B2

(12) United States Patent
Dorris et al.

(10) Patent No.: US 11,562,268 B2
(45) Date of Patent: Jan. 24, 2023

(54) ESTIMATING PHYSIOLOGICAL LOAD FROM LOCATION DATA

(71) Applicant: ZEBRA TECHNOLOGIES CORPORATION, Lincolnshire, IL (US)

(72) Inventors: Thomas Dorris, Frederick, MD (US); Carl S. Mower, San Jose, CA (US)

(73) Assignee: Zebra Technologies Corporation, Lincolnshire, IL (US)

(*) Notice: Subject to any disclaimer, the term of this patent is extended or adjusted under 35 U.S.C. 154(b) by 242 days.

(21) Appl. No.: 16/899,355

(22) Filed: Jun. 11, 2020

(65) Prior Publication Data

US 2021/0390425 A1    Dec. 16, 2021

(51) Int. Cl.
| | |
|---|---|
| *G01S 5/06* | (2006.01) |
| *G06N 5/04* | (2006.01) |
| *G06N 20/00* | (2019.01) |
| *G01S 5/02* | (2010.01) |
| *G06Q 50/28* | (2012.01) |

(52) U.S. Cl.
CPC ............. *G06N 5/04* (2013.01); *G01S 5/0226* (2013.01); *G01S 5/06* (2013.01); *G06N 20/00* (2019.01); *G06Q 50/28* (2013.01)

(58) Field of Classification Search
CPC .... G01S 5/0226; G01S 5/0231; G01S 5/0242; G01S 5/04; G01S 5/06; G01S 5/08; G01S 5/10; G01S 5/12; G01S 5/14; G01S 5/163; G01S 5/20; G01S 5/22; G06N 5/04; G06N 20/00; G06Q 50/28
See application file for complete search history.

(56) References Cited

U.S. PATENT DOCUMENTS

| | | | |
|---|---|---|---|
| 10,866,302 B2* | 12/2020 | Wu | H04W 4/33 |
| 2009/0102411 A1 | 4/2009 | Miller et al. | |
| 2010/0066669 A1 | 3/2010 | Amm et al. | |
| 2010/0191461 A1 | 7/2010 | Zeng | |
| 2014/0304107 A1* | 10/2014 | McAllister | G06Q 30/0631 705/26.7 |
| 2015/0186700 A1 | 7/2015 | Nikitin et al. | |
| 2018/0025412 A1* | 1/2018 | Chaubard | G06V 20/52 705/26.9 |
| 2020/0096599 A1* | 3/2020 | Hewett | G01S 5/0273 |
| 2020/0191943 A1* | 6/2020 | Wu | G01S 13/726 |
| 2021/0356493 A1* | 11/2021 | Mueggenborg | G08B 13/2417 |

OTHER PUBLICATIONS

International Search Report and Written Opinion for International Patent Application No. PCT/US2021/032405 dated Sep. 14, 2021.

* cited by examiner

*Primary Examiner* — Jean A Gelin

(57) ABSTRACT

Methods and devices for determining a load vector on an object are disclosed herein. An example method includes collecting location observations related to the object. The example method further includes filtering the location observations to determine an estimated model path. The example method further includes outputting a set of data from the estimated model path, wherein the set of data includes a model location, a model velocity, a model acceleration, and a model jerk. The example method further includes calculating a load vector from the set of data, scaling the load vector via a scaling index, and transmitting the scaled load vector to a remote device.

20 Claims, 10 Drawing Sheets

ESTIMATING PHYSIOLOGICAL LOAD FROM LOCATION DATA

BACKGROUND

Warehouses, retail spaces, hospitals, daycares, laboratories or other venues often employ Radio Frequency Identification (RFID) technology to track various objects located therein. Products, packages, vehicles, people, scanners, and robots may all be tagged with an RFID tag. For example, athletes playing competitive sports may have RFID tags embedded within their equipment. An RFID positioning system located in the venue (e.g., stadium) may then track the athletes' location as they traverse the venue. Receivers may be positioned throughout the venue, such as in overhead locations, on walls, or other surfaces, and operated to identify the RFID tags on the athletes moving throughout the venue.

The receivers are connected to a network host computer or server. The specific location of any particular athlete in the venue is typically determined by having the host computer process the payloads and capture data from a plurality of the receivers and using triangulation/trilateration techniques. A conventional host computer may then use this location data to calculate other physical quantities related to the athlete (e.g., velocity, acceleration). However, conventional systems fail to adequately interpret various physical quantities when determining an overall physiological load experienced by an athlete. Consequently, there is a need for techniques to efficiently and accurately determine overall physiological load based upon physical quantities.

SUMMARY

In an embodiment, the present invention is a system for determining a load vector on an object. The system comprises a receiver and a remote device. The receiver is configured to collect location observations related to the object, and filter the location observations to determine an estimated model path. The receiver is further configured to output a set of data from the estimated model path, wherein the set of data comprises a model location, a model velocity, a model acceleration, and a model jerk. The receiver is further configured to calculate a load vector from the set of data and scale the load vector via a scaling index. The user device is configured to receive the scaled load vector from the receiver and display the scaled load vector for viewing by a user.

In a variation of this embodiment, the receiver is further configured to transmit the scaled load vector by transmitting the set of data.

In another variation of this embodiment, the receiver collects the location observations from one or more of a memory, an identification tag, or a database.

In yet another variation of this embodiment, the receiver is further configured to determine the estimated model path using at least one of a Kalman filter, a linear regression, or a Fourier transform.

In still another variation of this embodiment, the remote device comprises at least one of an electronic display, a mobile device, or a module.

In still another variation of this embodiment, the receiver is configured to calculate the load vector from a directional load vector and a lateral load vector.

In yet another variation of this embodiment, the load vector is either a polar vector or a Cartesian vector, and wherein the Cartesian vector comprises a lateral load vector and a directional load vector with each having a magnitude and a direction.

In another embodiment, the present invention is a method for determining a load vector on an object. The method comprises collecting location observations related to the object; filtering the location observations to determine an estimated model path; outputting a set of data from the estimated model path, the set of data comprising: a model location, a model velocity, a model acceleration, and a model jerk; calculating a load vector from the set of data; scaling the load vector via a scaling index; and transmitting the scaled load vector to a remote device.

In a variation of this embodiment, transmitting the scaled load vector includes transmitting the set of data.

In another variation of this embodiment, the location observations are collected from one or more of a memory, an identification tag, or a database.

In yet another variation of this embodiment, the estimated model path is determined using at least one of a Kalman filter, a linear regression, or a Fourier transform.

In still another variation of this embodiment, the remote device comprises at least one of an electronic display, a mobile device, or a module.

In still another variation of this embodiment, the load vector is calculated from a directional load vector and a lateral load vector.

In yet another variation of this embodiment, the load vector is either a polar vector or a Cartesian vector, and wherein the Cartesian vector comprises a lateral load vector and a directional load vector with each having a magnitude and a direction.

In yet another embodiment, the present invention is a tangible machine-readable medium comprising instructions for determining a load vector on an object. When executed, the instructions cause a machine to at least collect location observations related to the object; filter the location observations to determine an estimated model path; output a set of data from the estimated model path, the set of data comprising: a model location, a model velocity, a model acceleration, and a model jerk; calculate a load vector from the set of data; scale the load vector via a scaling index; and transmit the scaled load vector to a remote device.

In a variation of this embodiment, transmitting the scaled load vector further includes transmitting the set of data.

In another variation of this embodiment, the location observations are collected from one or more of a memory, an identification tag, or a database, and wherein the remote device comprises at least one of an electronic display, a mobile device, or a module.

In yet another variation of this embodiment, determining the estimated model path includes using at least one of a Kalman filter, a linear regression, or a Fourier transform.

In still another variation of this embodiment, the load vector is calculated from a directional load vector and a lateral load vector.

In yet another variation of this embodiment, the load vector is either a polar vector or a Cartesian vector, and wherein the Cartesian vector comprises a lateral load vector and a directional load vector with each having a magnitude and a direction.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
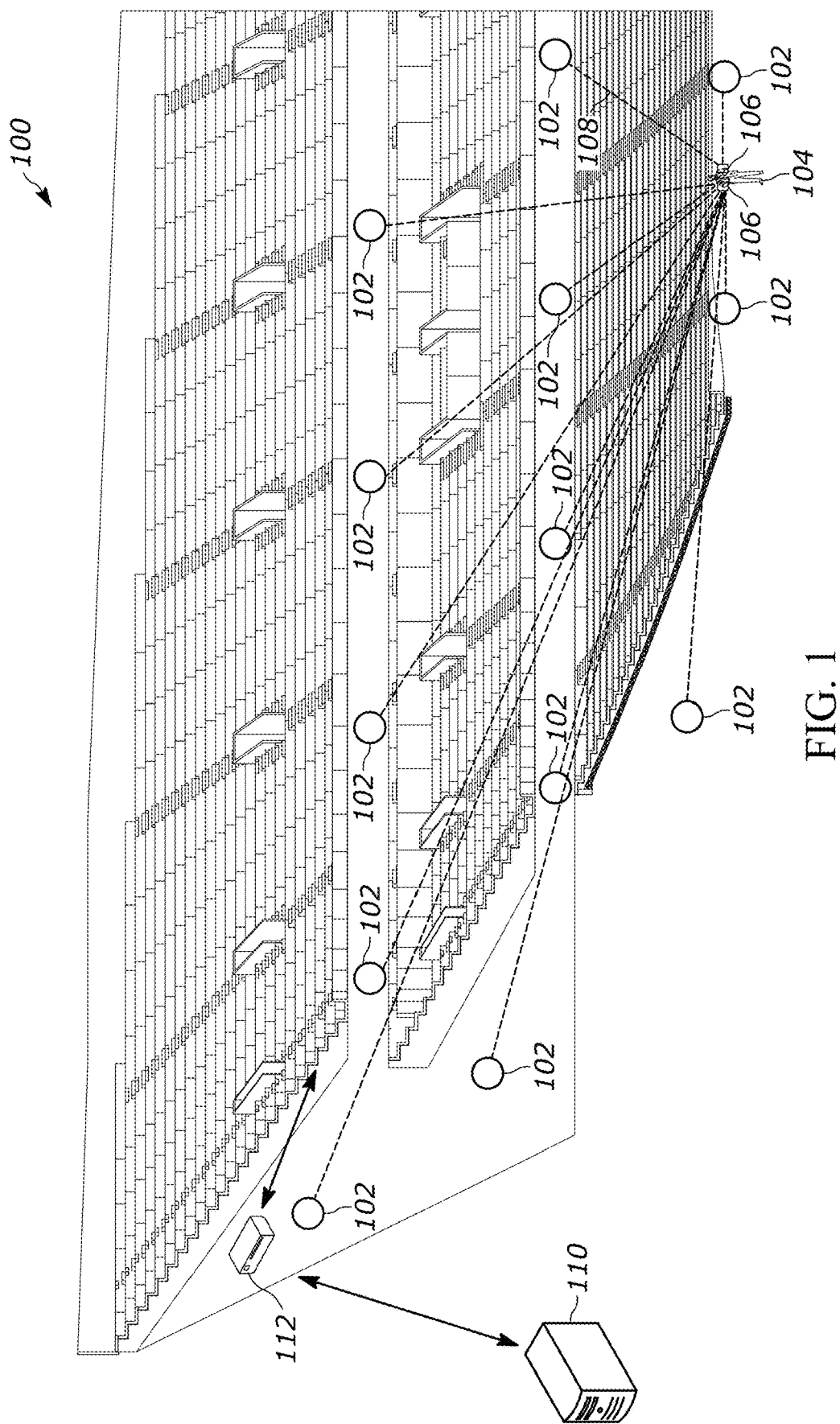
FIG. 1 illustrates an example venue in the form of a stadium in which moving objects may be located and tracked using receivers.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

RFID systems may be implemented using a plurality of overhead receivers, each receiver having one or more transceiver-based sensing units that identify targets in the venue. For example, these receivers may be RFID transceiver units that identify targets by identifying transmitters, such as RFID tags, associated with the targets. Generally, the receivers may receive position data from the RFID tags, which may be collectively analyzed to determine a position of the object via triangulation/trilateration. The receivers may receive a continuous stream of position data corresponding to the object, such that other physical parameters may be determined. For example, determining physiological load data may involve manipulating the stream of position data to determine other physical parameters associated with the object, such as velocity and acceleration. Based on the determined physiological load, operators/technicians can evaluate the amount of stress encountered by the targeted object (e.g. an athlete experiencing physical impact, muscular fatigue, joint torque, etc.).

Broadly speaking, the physiological load experienced by an object (e.g., athlete) at a point in time can be determined by evaluating each of the forces acting on the object at the point in time. For example, if an athlete is running forward and accelerates while making a turn, the athlete will experience both "directional" acceleration and "lateral" acceleration. As discussed herein, "directional" acceleration may refer to any load experienced by an object that is congruent with or directly opposes the object's direction of travel/motion. Further, "lateral" acceleration may refer to any load experienced by an object that is directed perpendicular to the object's direction of travel/motion.

However, acceleration by itself may be misleading. Without some concept of momentum at the time the acceleration event is observed, it may be unclear how impactful (e.g., the amount of load placed on the athlete) the event actually was. For example, it may be very difficult for an athlete who is currently running at nine to ten yards per second to accelerate at a rate of three yards per second squared. The athlete is likely running at or near their maximum speed, so any further acceleration may be considerably more difficult than it might be at lower speeds. Likewise, the impact of a deceleration scales with speed.

Problematically, traditional systems only calculate a single acceleration (e.g., "directional" acceleration) and fail to consider momentum when approximating the physiological load experienced by an athlete or other object. Such traditional systems may also organize acceleration "events" into a handful of bins (e.g., high, medium, or low acceleration) to characterize the physiological load experienced by the athlete. Moreover, traditional systems either provide no visible representation of the physiological load or a cluttered, indiscernible representation of the physiological load. Thus, traditional systems provide an imprecise, incomplete, and obtuse analysis of the physiological load experienced by an athlete during an acceleration "event."

Accordingly, the systems and methods of the present disclosure solve these and other issues with traditional systems. Namely, the techniques of the present disclosure generate a more precise and complete analysis of physiological loads experienced by athletes and other objects than traditional systems by gathering and incorporating data reflective of directional and lateral accelerations as well as momentum. The techniques of the present disclosure also provide a clear, insightful presentation format for the physiological load data that will improve a user experience with interpreting the physiological load data over the output of traditional systems.

Referring now to the figures, FIG. 1 depicts an example venue 100 in the form of a stadium in which receivers 102 may track and communicate with objects 104, shown in FIG. 1 as a person on the stadium field for simplicity, in accordance with the techniques described herein. More generally, the venue 100 may be any indoor or outdoor venue, and may have any layout or configuration. For example, although the example venue 100 is illustrated as a stadium, the disclosed embodiments may be implemented at other types of venues (such as a retail store, an airport, a warehouse, a performance center, a school, a hospital, etc.). Each object 104 is tagged with a mobile target 106 (referenced herein as an "identification chip" or "location tag"), such as a passive or active RFID product tag. The RFID product tag may be associated with a single object representative of one person (e.g., an athlete) or multiple persons (e.g., a particular team).

A multitude of the receivers 102 may be deployed in the venue 100. Each receiver 102 may be stationary and mounted at desired overhead positions or any other suitable location. Merely by way of example, the receivers 102 can be installed every twenty to eighty feet apart in a grid pattern, and may be located anywhere within the venue 100 (e.g., under stands, on-field locations). However, it will be appreciated that the exact number and spacing of receivers 102 may depend on the particular dimensions and layout of the venue 100, e.g., thirty, sixty, ninety, or more receivers 102 in a venue 100 spaced at a desired distance apart.

Each mobile target 106 may independently communicate with each of the receivers 102 via, for example, a tracking application or other networking interface configured to communicate with the receivers 102. Each receiver 102 may execute a read cycle to receive location data associated with objects 104 across communication channels 108. The communication channels 108 may be RF signals or any other suitable communication protocol. In some embodiments, the receivers 102 may include other sensing devices, such as an image sensor or an ultra-wideband (UWB) sensor.

A network computer or host server may be a centralized controller 110 configured to control each receiver 102. The example centralized controller 110 may be configured to determine and/or adjust the read cycles executed by the RFID readers within the receivers 102. Typically, the centralized controller 110 may be locally placed in a backroom at the venue 100, but the centralized controller 110 may be remote form the venue 100 (e.g., hosted in a cloud server). The centralized controller 110 may comprise one or more computers and may be in wired, wireless, direct, and/or networked communication with each receiver 102, for example, through a network switch 112. The centralized controller 110 may include a wireless RF transceiver that communicates with each receiver 102. For example, Wireless Fidelity (Wi-Fi) and Bluetooth® are open wireless standards for exchanging data between electronic devices that may be employed to allow the centralized controller 110 to communicate with each receiver 102. In other examples, the receivers 102 may be connected via Category 5 or 6 cables and use a suitable protocol for wired communications. Other embodiments may include receivers 102 that use a combination of wired and wireless communication. In still other examples, any of the functions of the centralized controller 110 described herein may be implemented at any one or more of the receivers 102.

The computer systems and receivers described herein may be connected via a communication network, which can include local and wide-area wireless networks, wired networks, or other IEEE 802.11 or Wi-Fi™ wireless communication systems, including virtual and extended virtual networks. It is envisioned that the communication network includes at least the centralized controller 110 and the receivers 102 that provide the operations described herein. It should be recognized that the present techniques could also be applied to any suitable wireless communication system. For example, the description that follows can apply to one or more communication networks that are IEEE 802.xx-based, employing wireless technologies such as IEEE's 802.11, 802.16, or 802.20, modified to implement embodiments of the present invention. The protocols and messaging needed to establish such networks are known in the art and will not be presented here for the sake of brevity.

FIG. 1 illustrates how knowing the accurate position of an object 104 in the venue 100 is important for estimating physiological load data. During the course of a typical event inside a stadium (e.g., venue 100) or other facility, many objects 104 may move within the stadium. For example, during a sporting event, athletes may move around to various positions on the stadium field. This movement may result in a wide variety of physiological loads exerted by and on the athletes. If any athletes are lost by the receivers 102, their movements may not be tracked, and any data concerning the physiological loads experienced by that player may be similarly lost. As a result, analytics companies and sports organizations may lose the opportunity to more fully understand the impacts athletic events have on the athletes. More generally, failing to track athlete movements (e.g., object 104 movements) may limit, if not eliminate, an empiric evaluation regarding the biomechanical effects of physical activity, which may lead to athletes suffering more injuries.

Figure 2:
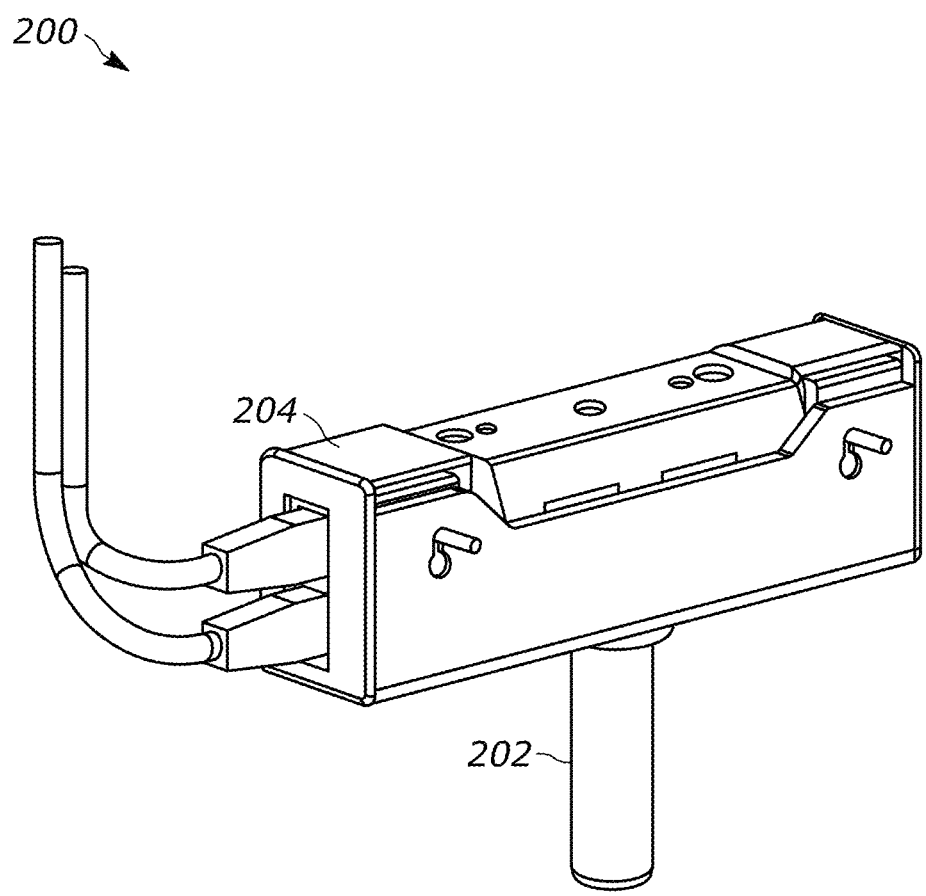
FIG. 2 is a perspective view of a receiver in FIG. 1, and in accordance with embodiments described herein.

FIG. 2 is a perspective view of an example receiver 200 capable of receiving position data corresponding to one or more RFID tags (e.g., mobile target 106) via an antenna 202. The example receiver 200 may be enclosed in a housing 204 that is mounted to a surface (e.g., ceiling, wall, support structure, etc.) within and/or near a stadium (e.g., venue 100). Generally, the housing 204 may be removably mounted to a surface to facilitate repositioning of the receiver 200, maintenance of the receiver 200, or any other suitable reason. Typically, however, the housing 204 may be mounted (e.g., during installation) to a surface using unmovable hardware, such that the antenna may not easily rotate, pivot, or otherwise move from the optimal orientation achieved at installation. In this manner, the receiver 200 may quickly and accurately locate and track moving objects within and/or near the corresponding stadium without interference from vibrations within the stadium due to heavy machinery or environmental conditions (e.g., thunderstorms, hail, earthquakes, etc.), HVAC systems, or direct physical contact with the receiver 200.

The example receiver 200 may additionally include a processor (not shown), and may communicate with a centralized controller (e.g., centralized controller 110) via a wired connection, wireless connection, and/or any other suitable type of connection or combination thereof. Generally, the antenna 202 may transmit RF beams to RFID tags on objects. The antenna 202 may then receive RF response signals from the RFID tags and may retransmit the RF response signals to the centralized controller. Alternatively, the RFID tags may include circuitry enabling them to actively transmit RF signals to the centralized controller without receiving an RF beam from the antenna 202. As illustrated, the antenna 202 may generally be oriented in a downward-facing direction towards the floor of the corresponding venue (e.g., venue 100) to optimally receive signals from the tagged objects below. However, it is to be appreciated that the antenna 202 may be oriented in any suitable fashion with respect to the venue in order to receive RF response signals from the RFID tags.

Figure 3A:
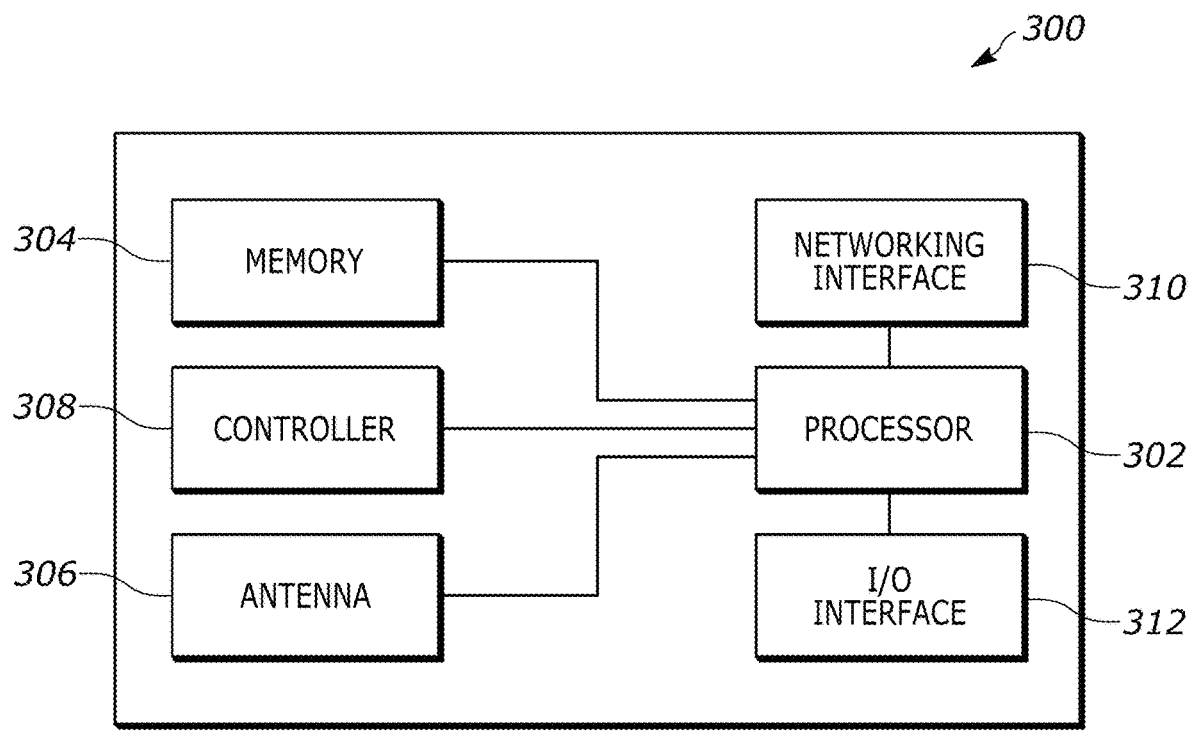
FIG. 3A is a block diagram representative of an example logic circuit capable of receiving and analyzing RFID tag signals, in accordance with embodiments described herein.

FIG. 3A is a block diagram representative of an example logic circuit capable of implementing, for example, one or more components of the example systems and specifically an example receiver 300 (e.g., receivers 102, 200). The example receiver 300 may generally capture location data from one or more RFID tags within a venue (e.g., venue 100). This location data may be transmitted to a controller (e.g., centralized controller 110) which receives location data from a plurality of the receivers, and subsequently used for triangulation and/or trilateration to determine locations of the RFID tags within the venue.

The example receiver 300 includes a processor 302, such as, for example, one or more microprocessors, controllers, and/or any suitable type of processor. The example receiver 300 further includes memory (e.g., volatile memory or non-volatile memory) 304 accessible by the processor 302, for example, via a memory controller (not shown). The example processor 302 interacts with the memory 304 to obtain, for example, machine-readable instructions stored in the memory 304.

Generally speaking, the example receiver 300 is operated, under the control of the processor 302, to transmit RF beams to the tags on the targets, and to receive RF response signals (and/or RF signals from active tags) from the tags, thereby interrogating and processing the payloads of the tags that are in a reading zone of the receiver 300. The RFID reading zone may be defined by the antenna 306 and controlled through beam steering by a controller 308. During operation, the example receiver 300 captures payload data or target data that identifies the tags and their associated products (e.g., objects 104). The controller 308 then controls the example receiver 300 to read the tags on the products in a reading mode of operation in accordance with a set of reading parameters.

The example receiver 300 may further include a network interface 310 to enable communication with other machines via, for example, one or more computer networks, such as a local area network (LAN) or a wide area network (WAN), e.g., the Internet. The network interface 310 may include any suitable type of communication interface(s) (e.g., wired and/or wireless interfaces) configured to operate in accordance with any suitable protocol(s), e.g., Ethernet for wired communications and/or IEEE 802.11 for wireless communications. For example, the processor 302 may communicate with a centralized controller through the network interface 310 to coordinate reading of RFID tags, and the processor 302 may provide the central controller with bearing information of an RFID tag for the central controller to determine the location of an RFID tag in a venue. Moreover, the example receiver 300 includes input/output (I/O) interfaces 312 to enable receipt of user input and communication of output data to the user, which may include, for example, any number of keyboards, mice, USB drives, optical drives, screens, touchscreens, etc.

Figure 3B:
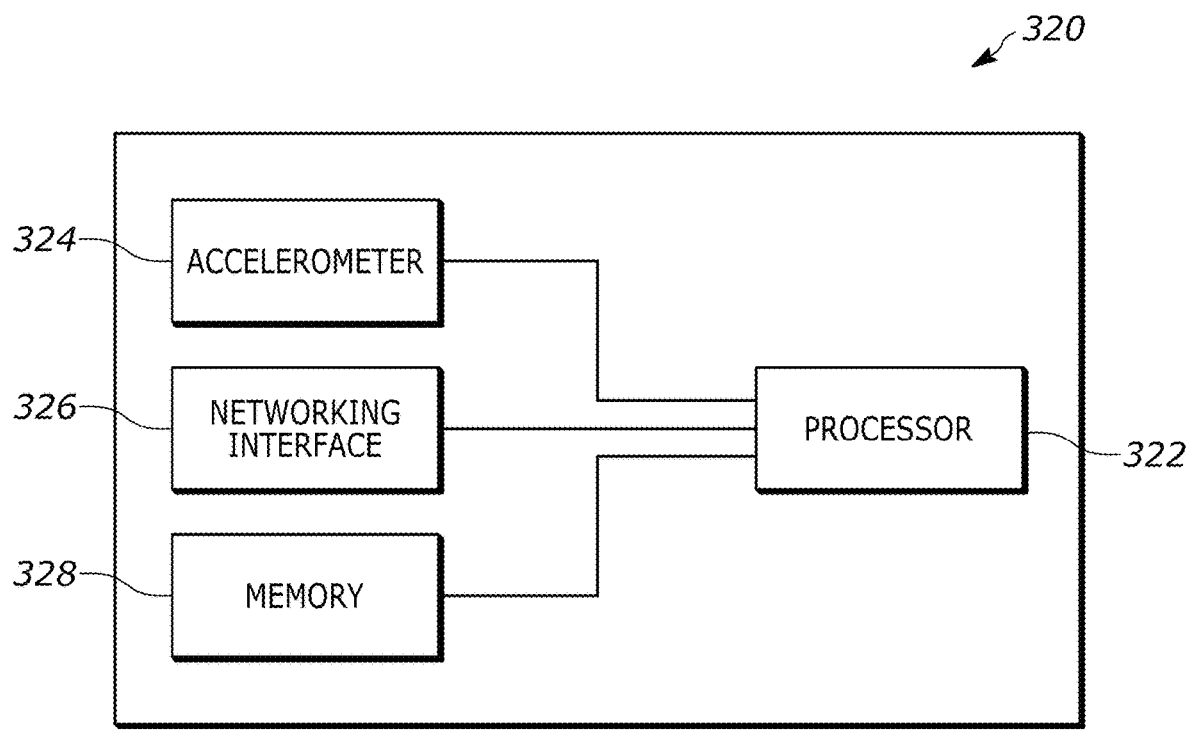
FIG. 3B is a block diagram representative of an example logic circuit capable of generating and transmitting RFID tag signals and acceleration signals, in accordance with embodiments described herein.

As mentioned, the example receiver 300 may include an antenna 306 operative for detecting and receiving an RFID tag signal to determine a static location of an object and/or the position of the object as it moves within a venue (e.g., venue 100). More particularly, the antenna 306 may transmit RF beams to objects, such as the example mobile target 320 illustrated in FIG. 3B. The example mobile target 320 may include a processor 322, an accelerometer 324, a networking interface 326, and a memory 328.

Generally, the example mobile target 320 may receive RF beams from Receivers, retrieve a RFID tag identification (ID) or other identifying information from memory 328, and transmit the identifying information in an RF response signal to the Receivers. More specifically, the example mobile target 320 may receive, via the network interface 326, RF beams from one or more Receivers, wherein the RF beams trigger the processor 322 to retrieve an RFID tag ID from memory 328. Alternatively, the example mobile target 320 may be an active RFID tag, such that the example mobile target 320 may, periodically and/or upon detecting a triggering event, transmit an RF signal to one or more Receivers. The RF signal may include the identifying information, as described herein.

Additionally or alternatively, the received RF beams may cause the processor 322 to retrieve acceleration data from the accelerometer 324. The acceleration data may include acceleration measurements made by the accelerometer during a duration D, and/or at a singular moment in time. More generally, the acceleration data may correspond to acceleration experienced by an object (e.g., object 104) during motion. For example, the object may be an athlete participating in an athletic event in a stadium (e.g., venue 100). The athlete may accelerate/decelerate as part of the athletic event, and as a result, the accelerometer 324 may generate acceleration data detailing the acceleration/deceleration experienced by the athlete during the athletic event. The accelerometer 324 may store the acceleration data in memory 328, and may be periodically or continuously accessed by the processor 322 in response to received RF beams. In embodiments, the accelerometer 324 may transmit the acceleration data directly to a receiver, via the network interface 326, where the acceleration data may be stored in memory 304 and/or analysed via the processor 302, as described herein. Moreover, it is to be appreciated that the all or part of the analysis described herein may be performed by the processor 322 and/or the processor 302 of the example receiver 300.

The network interface 326 of the example mobile target 320 may enable communication with other machines via, for example, one or more computer networks, such as a local area network (LAN) or a wide area network (WAN), e.g., the Internet. The network interface 326 may include any suitable type of communication interface(s) (e.g., wired and/or wireless interfaces) configured to operate in accordance with any suitable protocol(s), e.g., Ethernet for wired communications and/or IEEE 802.11 for wireless communications. For example, the processor 322 may communicate with one or more example receivers 300 through the network interface 326 to enable reading of the corresponding RFID tag, and the processor 322 may provide the one or more example receivers 300 with acceleration data associated with the RFID tag.

In this manner, the one or more example receivers 300 and/or a central controller (e.g., centralized controller 110) may determine the location of an object associated with an RFID tag in a venue. Broadly speaking, the arrangement for locating and tracking an object within a venue may include the controller 308 having one or more processors and one or more memories. The arrangement may include a plurality of Receivers deployed throughout a venue. Those receivers may, for example, be deployed in overhead positions throughout the venue. Further, in embodiments, both the example receiver 300 and the example mobile target 320 may include elements not illustrated in FIGS. 3A and 3B, respectively. For example, the example receiver 300 may include an RFID tag database which may store information associated with a plurality of RFID tags such as current locations of the plurality of RFID tags, a history of locations of the RFID tags, associated items or products physically coupled to the RFID tags, etc.

Figure 4:
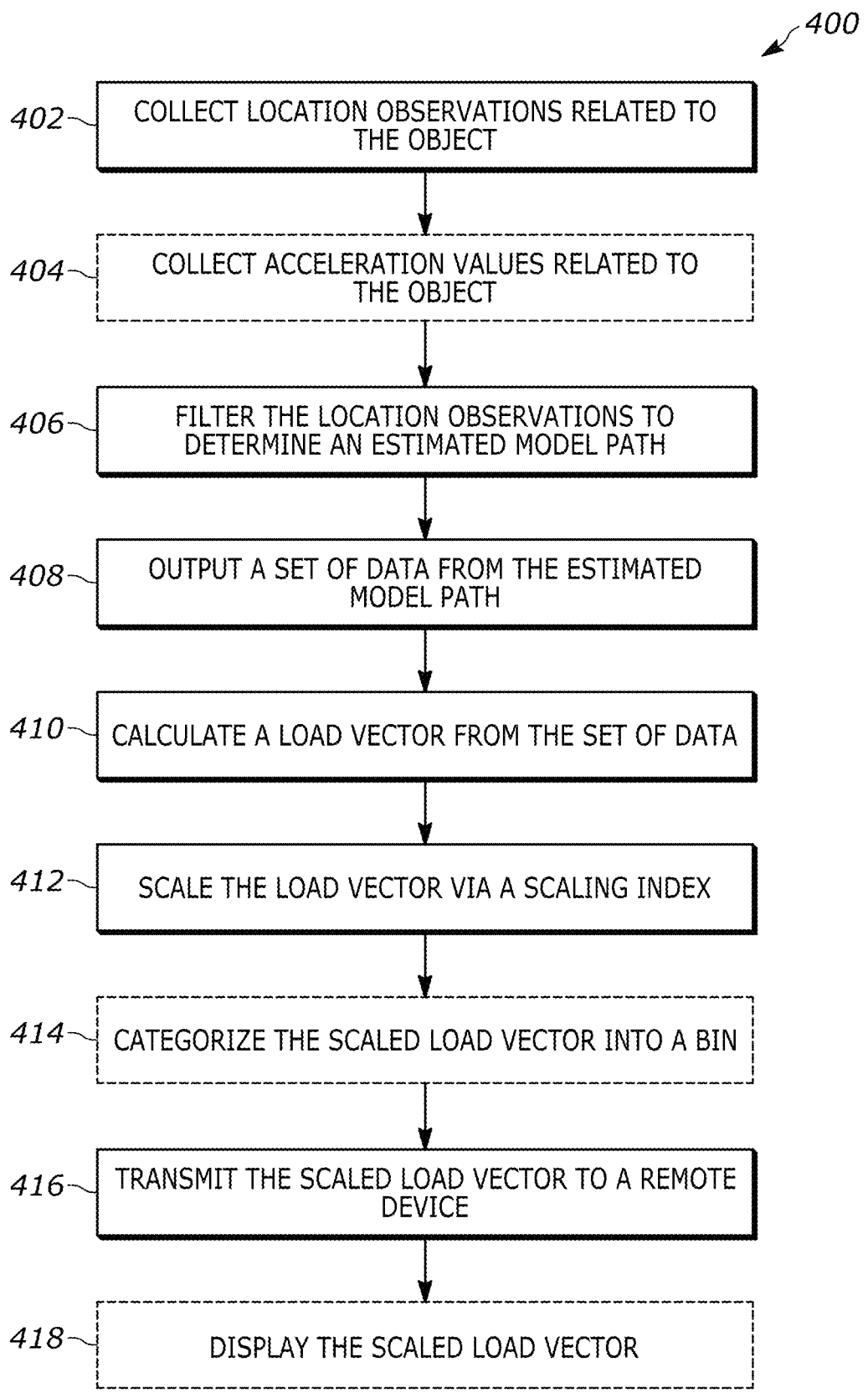
FIG. 4 is a flow diagram representative of a method for determining and displaying physiological load vectors, in accordance with embodiments described herein.
Figure 5:
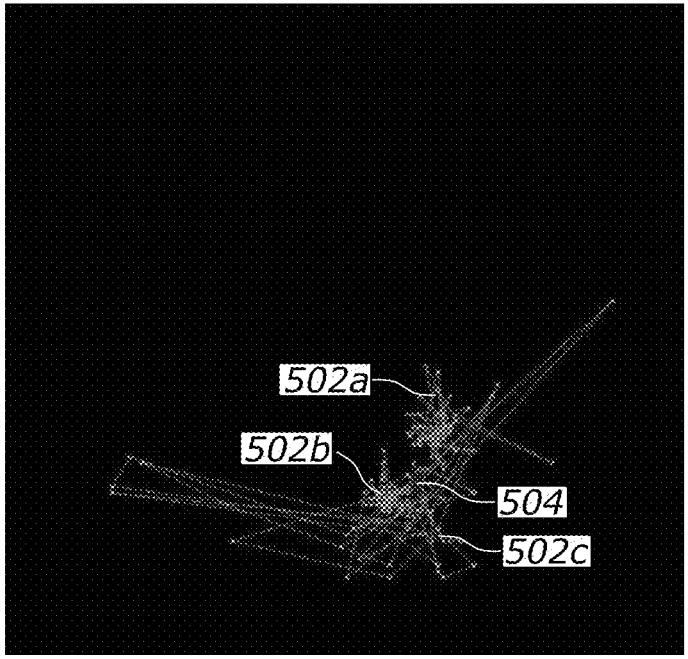
FIG. 5 is a comparative illustration of determined physiological load vectors during a rotation with/without the techniques described herein.
Figure 5:
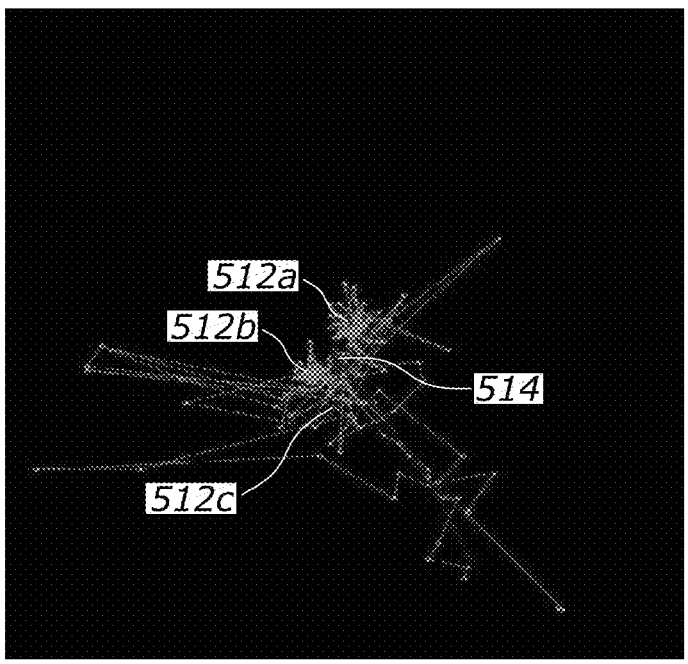
Figure 6:
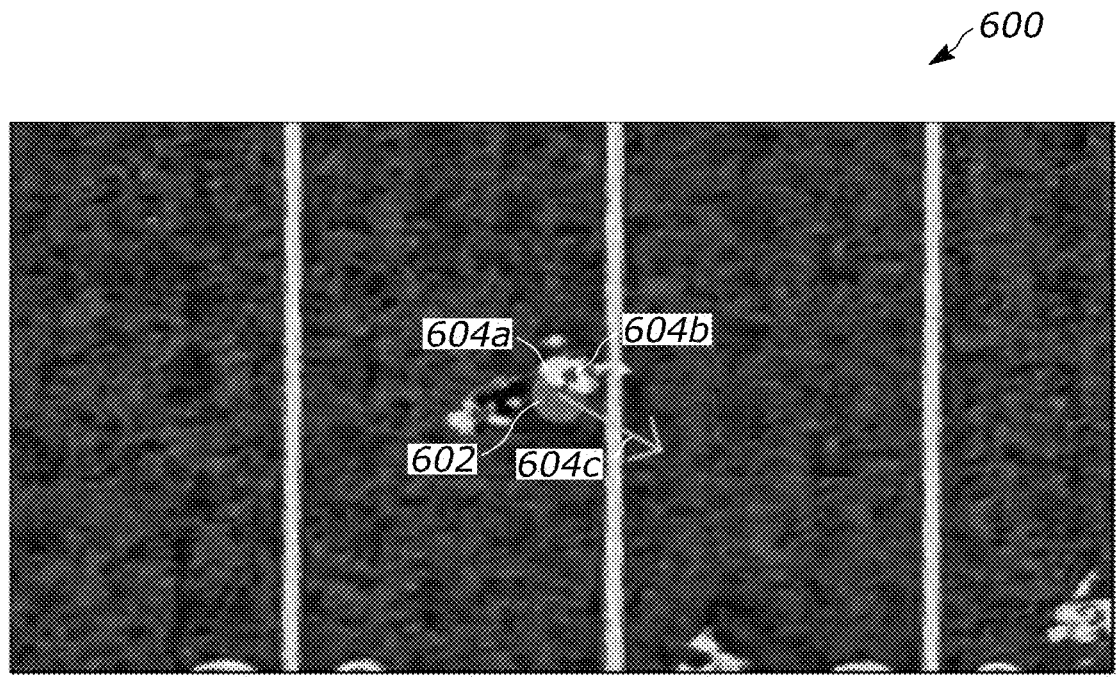
FIG. 6 depicts example scenarios of location observation tracker data and the corresponding position data determined using accelerometer data, in accordance with embodiments described herein.
Figure 6:
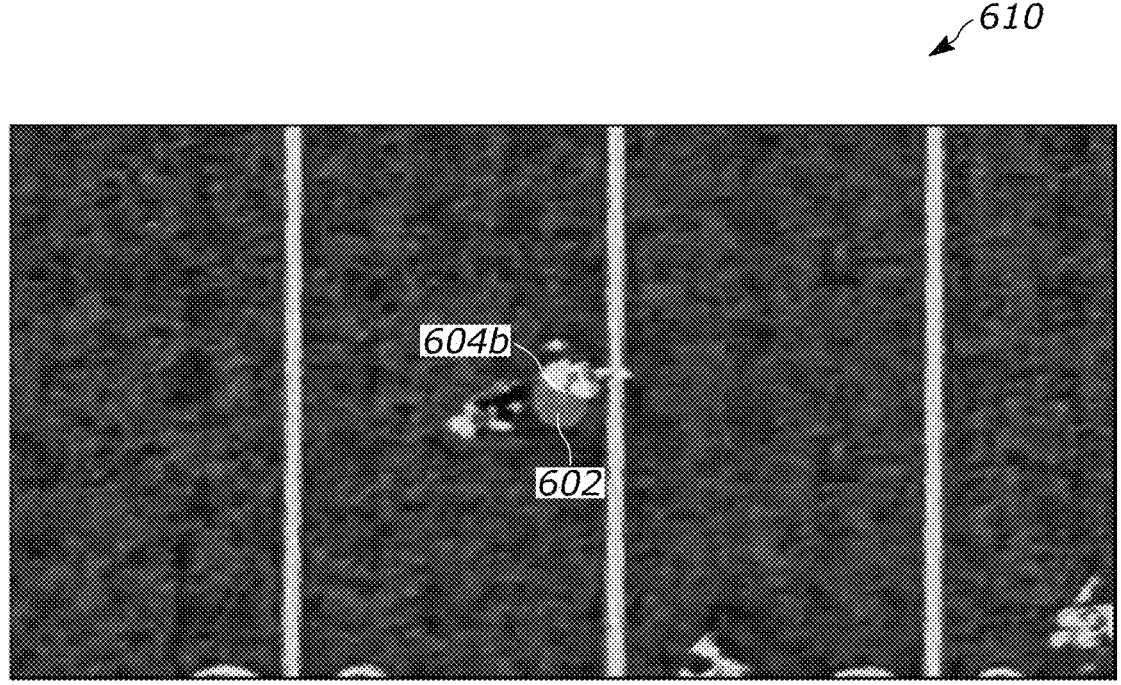

FIG. 4 is a flow diagram representative of an example method 400 for determining and displaying physiological load vectors (also referenced herein as "load vectors"). Generally, the example method 400 comprises collecting location observations (also referenced herein as "position values") and/or acceleration observations related to/associated with an object, calculating/scaling a physiological load vector based on the location observations, and transmitting/displaying the scaled load vector to/on a remote device. Collecting the location/acceleration observations is discussed below with additional reference to FIGS. 5 and 6. Calculating/scaling the physiological load vector is discussed below with additional reference to FIGS. 7A-7C. Transmitting/displaying the scaled load vector is discussed below with additional reference to FIG. 8. The example method 400 may be performed in whole or in part by, for example, a receiver (e.g., receiver 102, 200, 300) and/or a centralized controller (e.g., centralized controller 110).

Accordingly, the method 400 may begin by collecting position values related to the object (block 402). Generally speaking, a receiver and/or centralized controller may utilize RF response signals (or RF signals from an active RFID tag) received from an identification chip to determine/collect position values related to the associated object. The RF response signal may include an RFID tag number and/or other identification information to indicate to the receiver which RFID tag transmitted the RF response signal. The RF response signal may also include a timestamp indicating when the RF response signal was generated and/or transmitted from the RFID tag, and/or each receiver may generate a timestamp or an additional timestamp corresponding to a receipt time of the RF response signal. Additionally or alternatively, the RF response signal may include coordinate information or other position information to indicate to a relative position of the RFID tag with respect to a receiver.

In any event, the receiver may transmit the received RF response to a central controller or to other receivers for processing to determine the position values associated with the object. The receiver and/or central controller (e.g., centralized controller 110) may utilize triangulation and/or trilateration techniques to determine the position values associated with the object. For example, the central controller may receive RF response signals received at multiple receivers. The central controller may then analyse the timestamps corresponding to the transmission and receipt of each RF response signal to determine, via triangulation/trilateration, a position of the RFID tag.

The identification chip may generally be any suitable identification device and may be configured to communicate via any suitable frequency or protocol. For example, the identification chip may be an RFID tag (e.g., mobile target 106). In embodiments, the location observations may be collected from one or more of a memory, an identification tag, or a database. To illustrate, the receiver and/or centralized controller may retrieve historical position data related to the object to calculate and/or refine calculations performed with respect to the load vector(s) associated with the object, as described further herein. Block 402 may be performed by, for example, the processor 302 and/or the centralized controller 110.

The method 400 may then optionally continue by collecting acceleration values related to the object (optional block 404). As mentioned, an RFID tag (e.g., mobile target 320) may include an accelerometer (e.g., accelerometer 324) configured to generate acceleration data corresponding to the motion of the RFID tag. When an RFID tag receives an RF beam from a receiver, the RFID tag may include the acceleration data as part of the RF response signal. In other embodiments, the RFID tag is a beacon that sends RF signals comprising the acceleration data. For example, in an embodiment, the receivers may request/receive a constant stream of data from one or more RFID tags via RF response signals. This constant stream of data may be real-time to represent the current motion of an object or delayed to represent the motion of the target following a series of movements (e.g., following the end of a play/possession). Additionally or alternatively, the RFID tag may store position/motion data corresponding to the RFID tag and periodically transmit the RF response signal at a predetermined frequency. In either case, the RFID tag may additionally transmit the acceleration data with the position/motion data. As discussed further herein, the acceleration data may be used to, for example, indicate the beginning and/or the end of motion of a target (e.g., indicating when an athlete starts or stops). Optional block 404 may be performed by, for example, the processor 302 and/or the centralized controller 110.

Typically, the acceleration data may be coarse such that using the acceleration data to calculate speed or acceleration may be unfeasible or otherwise inaccurate. However, the acceleration data may help identify the moment an object (e.g., athlete) transitions from a stationary position to one of motion. This transition may be critical because the filtering parameters used to determine estimated model paths, as described herein, may change from a set of damped values used to reduce jitter for players standing still to a set of parameters that respond more quickly to players that are actually in motion. Moreover, the stationary-to-moving transition is very abrupt, so accurately and efficiently identifying and responding to the transition should be similarly abrupt.

For example, an American football player may have a location tag placed (e.g., mobile target 106) on each shoulder pad, and may additionally have a third tag placed at the base of the back of their neck, between the two shoulder tags. Each tag may have a 3-axis accelerometer providing acceleration data associated with the relative motion of the athlete. To illustrate, and in reference to FIG. 5, the example location outputs 500 may represent an athlete standing at the line of scrimmage prior to the beginning of a play. The example location outputs 500 may include sets of raw location outputs 502a, 502b, and 502c from each of three location tags attached to the athlete. Namely, the first set of raw location outputs 502a (illustrated as a set of light blue points) may correspond to location outputs from the right shoulder pad of the athlete. The second set of raw location outputs 502b (illustrated as a set of grey points) may correspond to location outputs from the left shoulder pad of the athlete. The third set of raw location outputs 502c (illustrated as a set of red points) may correspond to location outputs from the base of the back of the athlete's neck. The example location outputs 500 may additionally include a set of actual location outputs 504 (illustrated as a set of dark blue dots), representing the estimated actual motion of the athlete while standing at the line of scrimmage prior to the beginning of the play.

As depicted, the sets of raw location outputs 502a-c may include noise. Such noise may cause the resulting tracked output of a traditional system to wander in a manner that does not accurately represent the motion of the athlete as the traditional system may simply average the raw location data over time. By contrast and as further described herein, the present techniques and systems may receive/analyze acceleration data from the accelerometers included in each location tag to overcome this shortcoming of traditional systems. In this example, the athlete is simply standing around at the line of scrimmage prior to a play. As a result, the acceleration data may indicate that a minimal amount of movement is taking place with respect to the athlete.

Accordingly, the present techniques may fuse this acceleration data with the location data from each respective location tag to determine that the athlete's location is not drastically changing while standing at the line of scrimmage. The present techniques may then further determine that one or more of the location data points included in one or more of the sets of raw location outputs 502a-c are spurious as they do not accurately represent the motion/location of the athlete. As a result, the present techniques may also de-weight and/or otherwise de-emphasize those spurious locates as unlikely representing the true motion of the athlete.

As another example, the example location outputs 510 may represent an athlete actively moving in response to a play taking place. The example location outputs 510 may include sets of raw location outputs 512a, 512b, and 512c from each of three location tags attached to the athlete. Namely, the first set of raw location outputs 512a (illustrated as a set of light blue points) may correspond to location outputs from the right shoulder pad of the athlete. The second set of raw location outputs 512b (illustrated as a set of grey points) may correspond to location outputs from the left shoulder pad of the athlete. The third set of raw location outputs 512c (illustrated as a set of red points) may correspond to location outputs from the base of the back of the athlete's neck. The example location outputs 510 may additionally include a set of actual location outputs 514 (illustrated as a set of dark blue dots), representing the estimated actual motion of the athlete while actively moving in response to the play taking place.

Similar to the sets of raw location outputs 502a-c, the sets of raw location outputs 512a-c may include noise. However, in the scenario represented by the example location outputs 510, the accelerometers included as part of each location tag may register larger acceleration values and/or acceleration values that are otherwise indicative of an increase in the athlete's motion. This acceleration data may allow or otherwise trigger the systems of the present disclosure to change filter parameters and/or otherwise respond more aggressively to the sets of raw location outputs 512a-c that are further away from the athlete's current tracked position. As a result, the actual location outputs 514 may feature location data representing an athlete moving and/or otherwise deviating from their prior relatively static location. In this example, the actual location outputs 514 may include data points extending from the center of the example location outputs 510 to the bottom right of the example location outputs 510, indicating the athlete moving in response to the play taking place.

Thus, it is to be appreciated that using the accelerometer data as described above and herein may enable more accurate and responsive object location tracking and analysis. The accelerometer data may enable ignoring and/or otherwise de-emphasizing location data that suggests movement at times when the acceleration data suggests no movement, and may thereby minimize processing performed on the location data to increase processing efficiency and the overall accuracy of location data interpretation. Additionally, incorporating the accelerometer data into the location analysis may enable the present systems to more accurately respond to location data that suggests movement when the accelerometer data likewise suggests movement. As a result, the present systems and techniques may critically provide more accurate speed and acceleration data at the beginning of any motion without sacrificing stable location tracking while object is stationary.

Further, this acceleration data may help distinguish the impact of various types of physiological load vectors. For example, and in reference to the example scenario 600 illustrated in FIG. 6, an athlete 602 may run downfield during a play. At the end of the play, the athlete 602 may stop running and turn rapidly to begin walking from a downfield position back towards the huddle or sideline. Accordingly, the athlete 602 may have a relatively small forward acceleration 604a and forward velocity 604b and a relatively large lateral acceleration 604c. The relatively large lateral acceleration 604c corresponding to the athlete 602 turning at the end of a play does not correspond to a large physiological load because the athlete's 602 momentum (e.g., derived from the athlete's 602 velocity) and forward acceleration 604a are small. However, in traditional systems, such a large lateral acceleration 604c may be erroneously categorized as a high impact event indicating a large physiological load.

By contrast, the systems and techniques of the present disclosure may utilize the location observations and acceleration observations to generate load vectors consistent with the example scenario 610. The receiver and/or centralized controller may collect the location observations and acceleration observations to calculate the forward acceleration 604a, forward velocity 604b, and lateral acceleration 604c. As described further herein, the receiver and/or centralized controller may then use these three vectors 604a-c to calculate lateral and directional load vectors that the receiver and/or centralized controller may then display with the forward velocity vector 604b. As illustrated, the lateral and directional loads corresponding to the three vectors 604a-c may be very small. The receiver and/or centralized controller may additionally include threshold values for the lateral and directional loads, such that the lateral and directional loads calculated in the example scenario 610 are too small to satisfy the corresponding threshold values, and as a result, may not be displayed.

The method 400 may continue by filtering the location observations to determine an estimated model path (block 406). As previously mentioned, the raw location outputs (e.g., sets of raw location outputs 502a-c, 512a-c) may include noise that does not represent the actual position/motion of the object. This noise data should be excluded from the determination of the object's position/motion because it may cause an approximation of a motion/position approximation technique to deviate from the actual motion/position of the object. Thus, determining the actual motion of the object is not as trivial as simply connecting each of the raw location outputs based on their associated timestamps.

Broadly, determining the estimated model path includes predicting the future state of the object's motion/position based upon the most recent measurements of the object's motion/position. The estimated model path may then be compared to the measured values of the object to determine how accurately the estimated model path approximated the object's motion/position and to exclude any measured position observations that deviate from the estimated model path by more than a threshold amount. Any position observations that exceed the threshold amount may be excluded from a subsequent correction or other adjustment with respect to the estimated model path. Block 406 may be performed by, for example, the processor 302 and/or the centralized controller 110.

For example, a simplistic determination of the object's future position for a time t can be made in accordance with classical mechanics, given by:

$$x(t)=x_0+v_0 t+\tfrac{1}{2}at^2 \qquad (1)$$

where $x_0$ is the initial position of the object, $v_0$ is the initial velocity of the object, and a is the acceleration of the object. However, such a determination may not yield accurate predictions due to additional factors that may not be captured by the classical description presented in equation (1) (e.g., drag).

Thus, in embodiments, the estimated model path may be determined using at least one of a Kalman filter, a linear regression, or a Fourier transform. For example, a Kalman filter may filter the location observations by predicting the motion of the object, measuring the motion of the object, and correcting the predicted motion of the object. The prediction step of the Kalman filter may include a motion model that may vary based on entity type (e.g., athlete, ball, etc.), athlete position (e.g., center, wide receiver, etc.), and/or game state (e.g., pre-snap, in-flight, etc.). Generally, a motion model may be characterized by the following:

$$\frac{da}{dt} = -D(t)(2a + Dv) + \sigma_j \quad (2)$$

where D(t) represents the drag affecting the object at a time t, and $\sigma_j$ represents the motion uncertainty used to control any jitter experienced in the object's motion for a given situation. Moreover, these variables (also referenced herein as "filtering parameters") used in the Kalman filter may change and/or reset based upon a change in one or more characteristic of the object's motion. To illustrate, if an athlete transitions from carrying a ball (e.g., during a running play) to passing the ball through the air (e.g., during a passing play), the motion model of the ball may change to reflect the air drag affecting the ball's motion while in flight. For example, the drag filtering parameter may change to reflect the ball's flight by transitioning from a constant value to a variable value given by:

$$D(t) = k^* v(t)^2 \quad (3)$$

where k is proportional to the cross sectional area of the ball facing the flow of air and the drag coefficient of the air.

In any event, the receiver and/or centralized controller may then compare the estimated model path to the location observations after subsequent iterations of determining the estimated model path. The receiver and/or centralized controller may utilize a Kalman smoother and/or other smoothing technique to retroactively correct the estimated model path and/or location observations based on subsequently measured values. For example, the receiver and/or centralized controller may combine the estimated motion/position data from the motion model of equation (2) during a time period $\Delta t$ with the subsequently obtained location observations representing the actual motion/position of the object during the time period $\Delta t$. The receiver and/or centralized controller may then regenerate a position model for the object during the time period $\Delta t$ using both data sets to increase the overall accuracy of the resulting model.

The method 400 may continue by outputting a set of data from the estimated model path (block 408). The estimated model path represents the estimated changing position of the object during a respective time period. As a result, a variety of physical observables corresponding to the object may be determined based upon the estimated model path. For example, the set of data may include, without limitation, a model location, a model velocity, a model acceleration, and a model jerk. As used herein a term of the form "model_" may refer to any observable and/or other quantity calculated, retrieved, determined, and/or otherwise derived from the estimated model path. To illustrate, the model velocity may be the velocity of the object as derived from the position and time data included in the estimated model path. Block 408 may be performed by, for example, the processor 302 and/or the centralized controller 110.

The method 400 may continue by calculating a load vector from the set of data (block 410). Generally speaking, the physiological load experienced by any object may be characterized in terms of any internal/external forces exerted by and/or acting on the object. Namely, the power exerted on or by the object may provide a direct indication of the corresponding physiological load experienced by the object. Power may be defined as:

$$P = W/t \quad (4)$$

where P is the power received/output by the object, W is the work exerted on/by the object, and t is a unit of time. Power is not a directional quantity, and thus may not provide a differentiation between directional and lateral physiological loads experienced by an object. Block 410 may be performed by, for example, the processor 302 and/or the centralized controller 110.

Accordingly, a receiver and/or and RFID tag may record direction data included in the acceleration data prior to calculating the physiological load. Using the directional components of the acceleration and/or the velocity, the receiver and/or the centralized controller may determine one or more corresponding direction(s) of the physiological load vector. In embodiments, the receiver and/or centralized controller may then determine both a directional load vector and a lateral load vector using the directional information. In these embodiments, each physiological load vector may include a directional load vector and a lateral load vector. The directional load vector may represent a physiological load vector component in a forward direction or an opposing direction with respect to a reference frame of the object. The lateral load vector may represent a physiological load vector component in a right direction or a left direction with respect to the reference frame of the object.

For example, if the object is an athlete running on a field inside a stadium, the athlete may accelerate in a forward direction and/or decelerate in an opposing direction with respect to the athlete's frame of reference. Accordingly, in these embodiments, the receiver and/or centralized controller may calculate a directional load vector in the forward and/or opposing direction with respect to the athlete's reference frame. Similarly, if the athlete turns while running, the receiver and/or centralized controller may calculate a lateral load vector in the left and/or right direction with respect to the athlete's reference frame. It is to be appreciated that the acceleration, velocity, and/or the physiological load vector may have a negative value, indicating a direction opposite to the current motion of the object (e.g., the "opposing" direction).

Figure 7A:
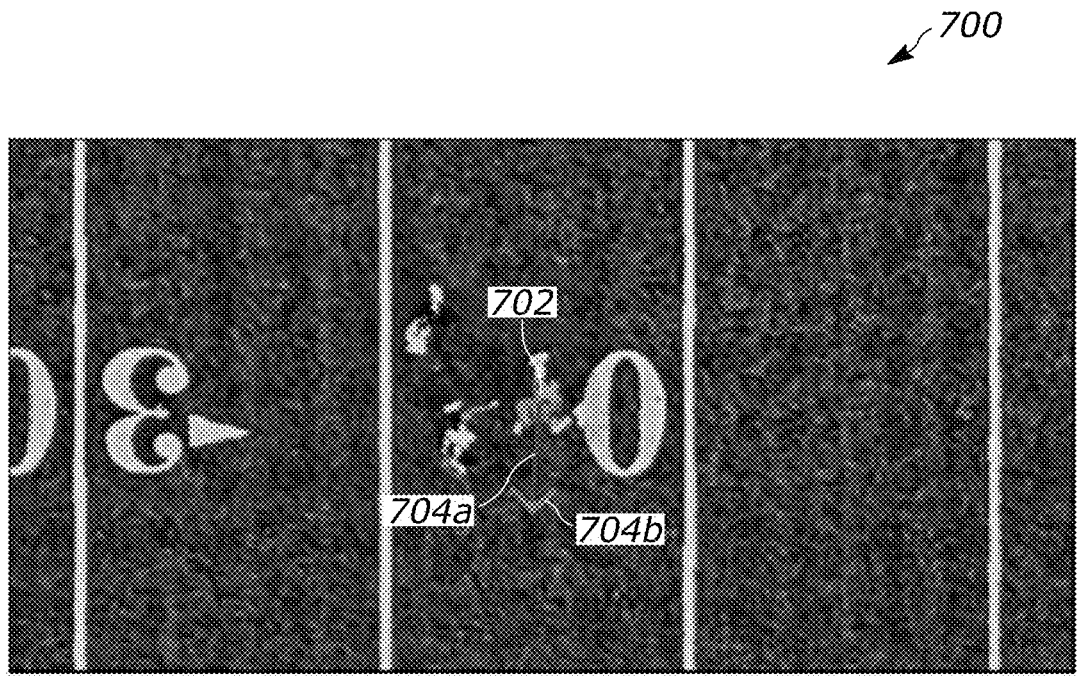
FIG. 7A is a comparative illustration of determined physiological load vectors during a unilateral acceleration with/without the techniques described herein.
Figure 7A:
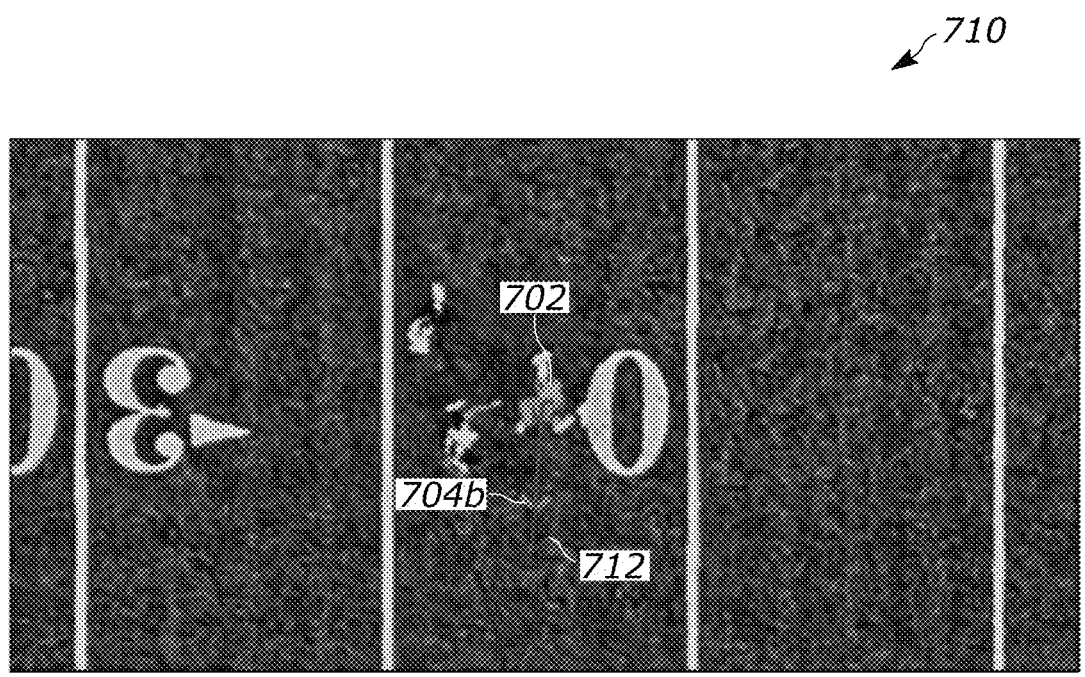

To illustrate, and in reference to FIG. 7A, the example scenario 700 depicts an athlete 702 during a "start of play" situation, where the athlete accelerates up to a maximum speed in a straight line. In this example scenario 700, the athlete's 702 efforts are almost fully focused on the athlete's 702 current direction of travel (e.g., forward). The athlete 702 may experience a directional acceleration in a forward direction with respect to the athlete's 702 reference frame, as represented by the directional acceleration vector 704a. The athlete 702 may also experience a corresponding velocity in the forward direction with respect to the athlete's 702 reference frame, as represented by the velocity vector 704b. As a result, the directional acceleration vector 704a may be positive, indicating that the acceleration is in the same direction as the velocity vector 704b. It is to be understood that the vector length of each vector depicted in each illustration described herein is proportional to the magnitude of the quantity the vector represents. For example, a shorter vector represents a value (e.g., acceleration) with a relatively smaller magnitude than a longer vector representative of the same value.

In embodiments, the directional and lateral load vectors may each be represented with a magnitude and a direction in a Cartesian coordinate system (e.g., $\hat{x}$, $\hat{y}$, and $\hat{z}$ unit vector components) and/or using any other suitable metric. Additionally or alternatively, the directional and lateral load vectors may be represented in a polar/spherical coordinate system, where the directional and the lateral load vectors may each have a respective angle(s) (e.g., $\theta$ and/or $\phi$ angle(s) with respect to a unit circle) and a respective magnitude. The receiver and/or centralized controller may then combine or otherwise utilize the directional load vector and the lateral load vector to calculate the load vector.

Problematically, power calculated in accordance with equation (4) is dependent upon the mass of the object. Typically, however, the mass of each object is not included as part of the RF response signals generated by the RFID tag associated with each object. Including such information into signals generated by the RFID tag may result in discrepancies between different data sets. For example, if an RFID tag is configured to transmit RF response signals corresponding to a particular object (e.g., by including mass values with position/acceleration data) and the RFID tag is placed on another object, the resulting data may be irreparably skewed. Moreover, incorporating the object mass into the RF response signals may cause problems if the mass of the object changes over time (e.g., an athlete gains or loses weight). Accordingly, the conventional definition of power may be modified to yield a mass-independent "load," given by:

$$L = a \cdot v \qquad (5)$$

where a is the acceleration of the object, and v is the velocity of the object. As mentioned, the receiver (e.g., via processor 302) or a centralized controller may calculate the velocity values based on the location observations received from the RFID tag (block 402), and may receive the acceleration data from an accelerometer (e.g., accelerometer 324) and/or based upon the location observations.

By excluding the mass of the object from the load calculation, the resulting load vector may be object independent. For example, a first object with a mass of one-hundred kilograms moving at a first acceleration for a first duration may have a power output (e.g., calculated in accordance with equation (4)) one-hundred times greater than a second object with a mass of one kilogram moving at the first acceleration for the first duration. However, using the load described by equation (5), the first object may have a load vector equivalent to the second object. The load vector(s) for each object may then be evaluated based purely on the motion of the objects, instead of basing the evaluation on the specific object corresponding to the load vector(s). As discussed further herein, this enables the creation of a scaled load metric capable of identifying the relative load experienced by an object regardless of the physical quantities corresponding to the object (e.g., the object's size, shape, mass, etc.).

The method 400 may continue by scaling the load vector via a scaling index (block 412). Generally speaking, the load vector calculated at block 410 is not expressed in "traditional" units of power, and as a result, may lead to interpretation difficulties if not scaled in a manner that is readily understandable. The scaling index resolves this potential interpretation difficulty by providing a readily understandable scaling system. The scaling index may generally refer to a load value that represents the maximum load an object could be expected to generate or otherwise experience. In embodiments where the object is a human (e.g., an athlete), the scaling index may represent the maximum load a human could be expected to generate under their own power. Block 412 may be performed by, for example, the processor 302 and/or the centralized controller 110.

To illustrate, the scaling index may represent a load calculated in accordance with equation (5) of a world-class athlete performing at maximum effort. For example, an elite sprinter may be expected to perform at essentially the maximum effort a human can generate to move in a single direction during the one-hundred meter dash. In this example, the elite sprinter may have a body weight of 93.9 kilograms and produce a peak power output of 2619.5 watts. Dividing the sprinter's peak power output by their body weight may yield a scaling index of 27.9, in accordance with the load definition provided by equation (5). In embodiments, the directional load and the lateral load may each have an associated scaling index.

Using this scaling index, the receiver and/or centralized controller may compare each calculated load vector to the scaling index to determine a scaled load vector. For example, the receiver and/or centralized controller may divide the calculated load vector by the scaling index to determine the scaled load vector. As previously mentioned, the load vector may be negative to represent forces generated by and/or otherwise operating on the object in an opposing direction to the object's direction of motion. Thus, the scaled load vector may range from −1 to 1 or from any other desired range of values, such as −100 to 100. To illustrate, if an athlete runs during the course of a play and generates, in accordance with equation (5), a maximum load vector of 20 during the play, the scaled load vector corresponding to the athlete's motion is approximately 0.717. In this example, the scaled load vector may indicate that the athlete generated a load roughly 72% of the maximum load expected from a human during the play.

Occasionally, the scaled load vector may fall outside the range of scaled load vector values because the scaling index is calculated based upon the maximum load an object may be expected to generate and/or otherwise experience. As a result, it is possible that the calculated load vector may exceed the scaling index if the load generated by and/or otherwise experienced by an object exceeds the load that was thought to be the maximum the object could generate and/or otherwise experience. In reference to the above example, another elite sprinter may run the one-hundred meter dash faster than the previous sprinter, and as a result, may produce a higher peak power output (e.g., 2700 watts) at a similar body weight (e.g., 94 kilograms). This higher peak power output may then be converted to a load vector in accordance with equation (5), to yield a new scaling index of approximately 28.7.

Referring again to FIG. 7A, the example scenario 710 depicts the impact the scaled load vector may have on the interpretation of a particular play. The athlete 702 is again depicted in the "start of play" situation, where the athlete accelerates up to a maximum speed in a straight line. The athlete 702 may experience the same directional acceleration represented by the directional acceleration vector 704a in the example scenario 700, and the corresponding velocity represented by the velocity vector 704b. The receiver and/or centralized controller may utilize both the acceleration and velocity to calculate the directional load vector 712, in accordance with equation (5). In this case, the directional acceleration vector 704a and velocity vector 704b are substantially parallel, so the lateral load vector (not shown) may be substantially zero.

As illustrated, the directional load vector 704a may be positive, and may have a magnitude significantly greater than either the velocity vector 704b or the directional acceleration vector 704a. Traditional systems may interpret the relatively small magnitude of the directional acceleration vector 704a as an indication that the physiological load experienced by the athlete is relatively minimal. By contrast, when calculated in accordance with equation (5), the directional load vector 712 indicates that the physiological load experienced by the athlete is substantial. Namely, because the athlete 702 has an initial velocity in addition to their acceleration, the load generated by the athlete to accelerate at the given rate is greater than the load required to accelerate at that rate from a motionless state. Thus, the directional load vector 712 calculated in accordance with equation (5) provides a more accurate representation of the load generated by the athlete 702 during the "start of play" illustrated in the example scenario 710 than traditional systems.

Figure 7B:
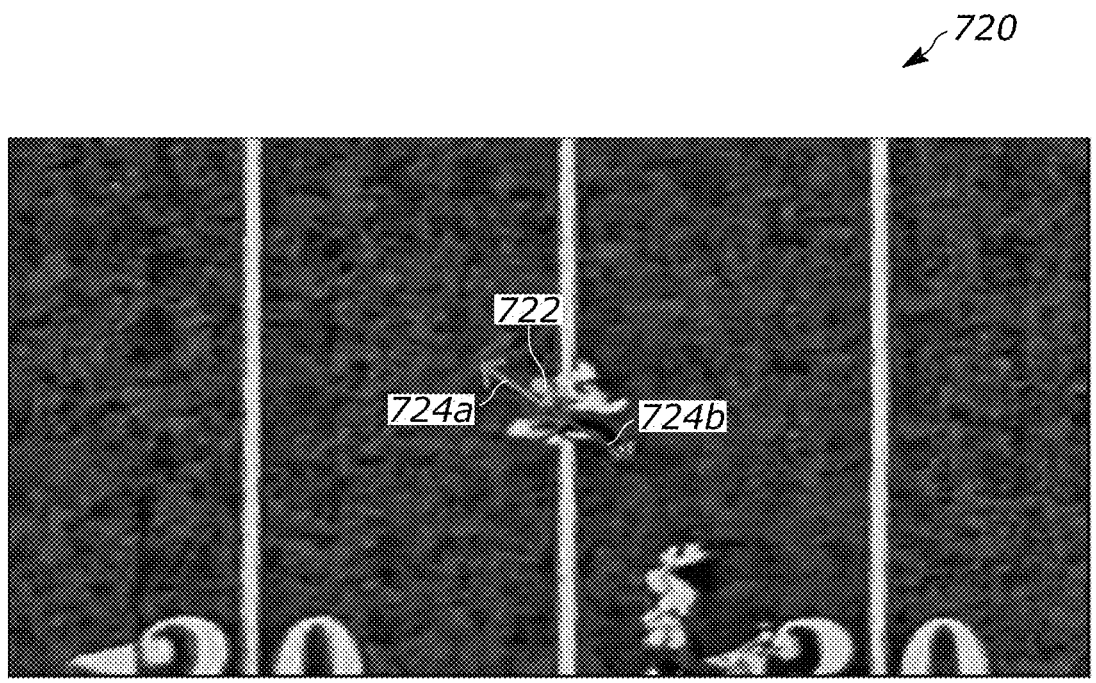
FIG. 7B is a comparative illustration of determined physiological load vectors during a unilateral deceleration with/without the techniques described herein.
Figure 7B:
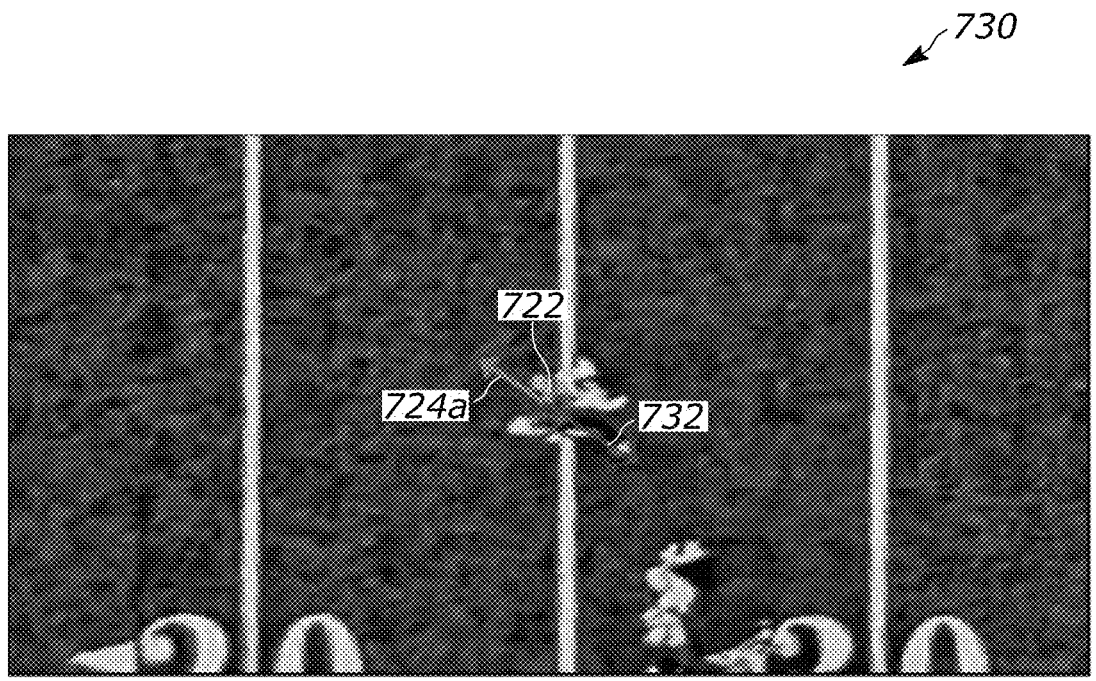

As another example, and in reference to FIG. 7B, the example scenario 720 illustrates an athlete 722 in an "end of play" situation. The athlete 722 may be running in a direction as indicated by the velocity vector 724a, and may begin slowing their speed at the end of the play, as indicated by the directional acceleration vector 724b. The directional acceleration vector 724b may be negative in this example scenario 720, indicating that the slowing force generated by the athlete is acting in the opposite direction of the athlete's motion (e.g., the direction of the velocity vector 724a).

Additionally, the example scenario 730 illustrates the same "end of play" situation involving the athlete 722, as evaluated in accordance with equation (5). The receiver and/or centralized controller may utilize both the velocity vector 724a and the directional acceleration vector 724b to determine the directional load vector 732. Similar to the "start of play" situation depicted in FIG. 7A, the directional acceleration vector 724b and velocity vector 724a are substantially parallel in opposing directions, so the lateral load vector (not shown) may be substantially zero. The directional load vector 732 may have a direction and magnitude similar to the directional acceleration vector 724b because the directional acceleration vector 724b is in an opposing direction to the velocity vector 724a and the athlete 722 may not have a high velocity at the end of a play.

Figure 7C:
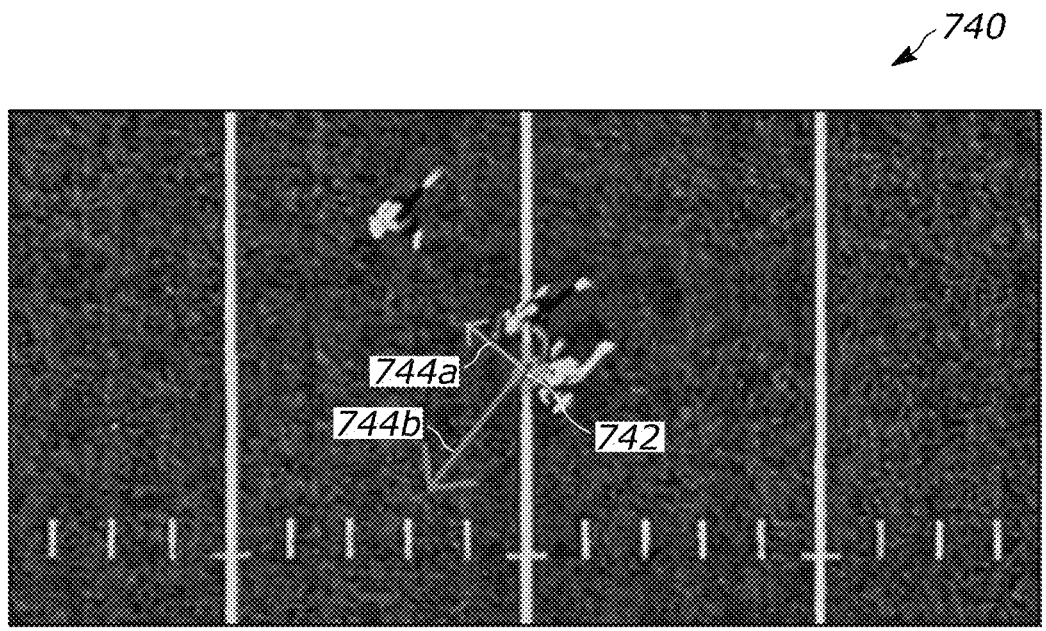
FIG. 7C is a comparative illustration of determined physiological load vectors during a multilateral acceleration with/without the techniques described herein.
Figure 7C:
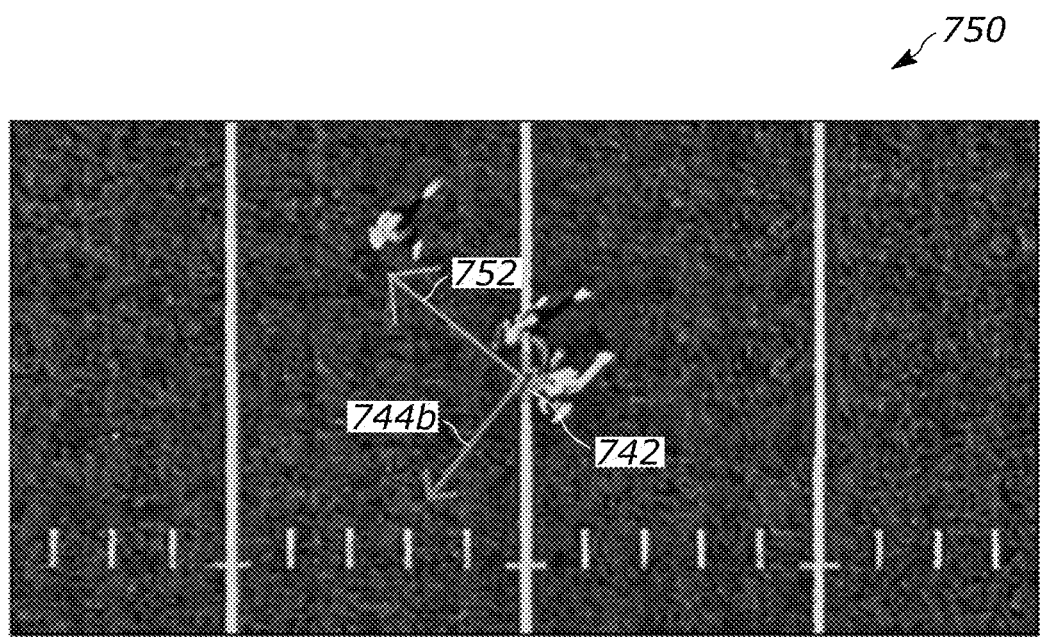

As yet another example, and in reference to FIG. 7C, the example scenario 740 illustrates an athlete 742 in a "mid-play" situation. In this example scenario 740, the athlete 742 may be changing their direction of travel, as indicated by the lateral acceleration vector 744a, while running at near maximum speed, as indicated by the velocity vector 744b. The athlete 742 may not change their directional velocity as a result of the turn, and may therefore not have any directional acceleration. Traditional systems typically evaluate physiological load based upon the directional acceleration an object (e.g., athlete) generates and/or otherwise experiences, so a traditional system would likely conclude that a relatively little amount of load was generated as a result of the turn executed by the athlete 742 in the example scenario 740.

However, contrary to this evaluation, as the athlete 742 pushes against their established momentum to alter their direction of travel, the athlete 742 may generate a significant amount of load. The change in direction is attributable to the athlete's 742 lateral acceleration, which may act as a side-load to the athlete. Namely, the lateral acceleration may neither increase or decrease the athlete's 742 rate of motion (e.g., velocity), but may instead redirect the athlete's 742 motion.

Accordingly, the example scenario 750 illustrates the same "mid-play" situation involving the athlete 742, as evaluated in accordance with equation (5). The receiver and/or centralized controller may utilize both the velocity vector 744b and the lateral acceleration vector 744a to determine the lateral load vector 752. The lateral acceleration vector 744a and the velocity vector 744b are substantially perpendicular, so the directional load vector (not shown) may be substantially zero. The lateral load vector 752 may have a direction similar to the lateral acceleration vector 744a because the lateral acceleration vector 744a is responsible for the lateral load generated by the athlete 742.

However, similar to the "start of play" situation illustrated in FIG. 7A, the lateral load vector 752 may have a magnitude significantly greater than the lateral acceleration vector 774a. Namely, because the athlete 742 has an initial velocity in addition to their acceleration, the load generated by the athlete to accelerate at the given rate is greater than the load required to accelerate at that rate from a motionless state. More generally, the load the athlete 742 must generate to change direction scales with their velocity in accordance with equation (5). The velocity vector 744b in the "mid-play" situation of FIG. 7C represents the athlete 742 running at their near maximum speed. At the athlete's 742 maximum speed, any change in direction may require the athlete 742 generating a relatively large amount of lateral load. Thus, the lateral load vector 752 calculated in accordance with equation (5) may provide a more accurate representation of the load generated by the athlete 742 during the "mid-play" situation illustrated in the example scenario 750 than traditional systems.

The method 400 may optionally continue by categorizing the scaled load vector into one or more bins (optional block 414). The one or more bins may generally describe the relative magnitude of the scaled load vector. For example, the one or more bins may include (i) a high load bin, (ii) a medium load bin, (iii) a low load bin, and/or (iv) a no-load bin. Optional block 414 may be performed by, for example, the processor 302 and/or the centralized controller 110.

The high load bin may correspond to scaled load vectors with magnitudes falling within the highest quartile of scaled load values. For example, if scaled load vectors generally fall within a range from −100 to 100, the high load bin may represent all scaled load vectors with magnitude values greater than 100 to 75 and from −75 to all values less than −100. The medium load bin may correspond to scaled load vectors with magnitudes falling within a middle quartile of scaled load values. For example, if scaled load vectors generally fall within a range from −100 to 100, the medium load bin may represent all scaled load vectors with magnitude values from 75 to 50 and from −50 to −75. The low load bin may correspond to scaled load vectors with magnitudes falling within another middle quartile of scaled load values. For example, if scaled load vectors generally fall within a range from −100 to 100, the low load bin may represent all scaled load vectors with magnitude values from 50 to 25 and from −25 to −50. The no load bin may correspond to scaled load vectors with magnitudes falling within the lowest quartile of scaled load values. For example, if scaled load vectors generally fall within a range from −100 to 100, the no load bin may represent all scaled load vectors with magnitude values from 25 to −25.

In embodiments, the receiver and/or centralized controller may train a machine learning model to calculate, scale, and categorize the load vector. For example, the receiver and/or centralized controller may use (i) a set of prior location observations, (ii) a maximum load the object may be expected to generate and/or otherwise experience, and (iii) a set of prior bin categorizations. Moreover, in these embodiments, the receiver and/or centralized controller may apply the machine learning model to the collected location observations to calculate, scale, and categorize the load vector. It is to be appreciated that the receiver and/or centralized controller may train and/or apply the machine learning model to perform all or some of the calculating, scaling, categorizing, and/or other actions described herein with respect to the load vector(s).

The method 400 may then continue by transmitting the scaled load vector to a remote device (block 416). Generally, the remote device may be a device capable of receiving the scaled load vectors from the receiver and/or the centralized controller. Typically, the receiver and/or centralized controller may transmit the scaled load vector to the remote device to allow a user of the remote device to view, acknowledge, and/or otherwise interact with the scaled load vector and any corresponding data. Accordingly, the remote device may typically include a user interface or other display configured to display the scaled load vector and/or other corresponding data to the remote device user. Block 416 may be performed by, for example, the processor 302 and/or the centralized controller 110.

In embodiments, transmitting the scaled load vector may further include transmitting the set of data, and the remote device may comprise at least one of an electronic display, a mobile device, or a module. Moreover, it will be appreciated that the receiver and/or centralized controller may transmit the scaled load vector to the remote device via a hardwired connection or via a wireless network, which may include local and wide-area wireless networks, wired networks, or other IEEE 802.11 or Wi-Fi™ wireless communication systems, including virtual and extended virtual networks.

The method 400 may optionally continue by displaying the scaled load vector for viewing by a user (optional block 418). Generally, the remote device may display the scaled load vector after receiving the scaled load vector from the receiver and/or centralized controller. Displaying the scaled load vector may allow the user to analyze or otherwise interpret the scaled load vector. In this manner, the user may develop an understanding of the loads generated by and/or otherwise experienced by the objects of interest (e.g., athletes) to compare relative load outputs over time and in a wide variety of situations. In embodiments, displaying the one or more physiological values in one or more of (i) a radar-type display, (ii) a vector-type display, or (iii) a heat map display. Optional block 418 may be performed by, for example, the processor 302 and/or the centralized controller 110.

Figure 8:
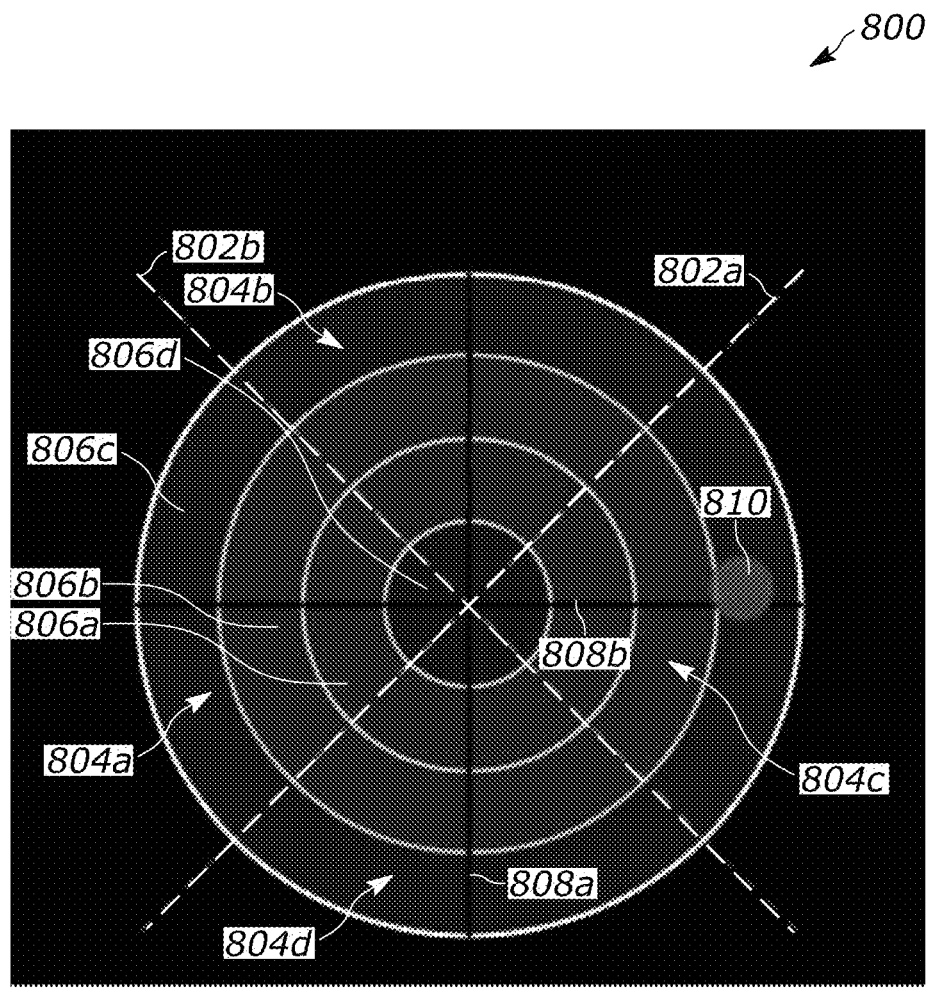
FIG. 8 is an example illustration of a radar-type display of physiological load vectors, in accordance with embodiments described herein.

For example, and in reference to FIG. 8, the remote device may display the scaled load vector in a manner similar to the radar-type display 800. The radar-type display 800 may include load vector dividing lines 802a, 802b that delineate between lateral load sections 804a, 804c and directional load sections 804b, 804d. Each of the lateral load sections 804a, 804c and directional load sections 804b, 804d may be segmented by load bin segments 806a, 806b, 806c, and 806d. The load bin segments 806a-d may each correspond to a particular range of scaled load vector magnitude values. To illustrate, the low bin segment 806a, the medium bin segment 806b, the high bin segment 806c, and the no load bin segment 806d may correspond to the low load bin, the medium load bin, the high load bin, and the no load bin, respectively, from the categorization discussed with respect to optional block 414.

The radar-type display 800 may also include reference frame axes 808a, 808b, corresponding to the object's reference frame. The reference frame axes 808a, 808b may establish the direction of any scaled load vectors with respect to the object, such that any scaled vector appearing on the radar-type display 800 below the second reference frame axis 808b may be a load in the opposing direction of the object's motion. Similarly, any scaled vector appearing on the radar-type display 800 to the left of the first reference frame axis 808a may be a load acting or generated by the object in a leftward direction with respect to the object's direction of motion. For example, the scaled vector 810 appears on the display to the right of the first reference frame axis 808a and slightly above the second reference frame axis 808b. Accordingly, the scaled vector 810 may represent a high lateral load in a primarily rightward (e.g., lateral) direction and slightly in the forward direction (e.g., directional) of the object's motion.

The above descriptions refers to the accompanying drawings. Alternative implementations of the examples represented by the block diagrams and figures include one or more additional or alternative elements, processes and/or devices. Additionally or alternatively, one or more of the example block of the diagrams or elements of the figures may be combined, divided, re-arranged or omitted. Components represented by the blocks of the diagrams and elements of the figures are implemented by hardware, software, firmware, and/or any combination of hardware, software and/or firmware. In some examples, at least one of the components represented by the blocks of elements of the figures is implemented by a logic circuit. As used herein, the term "logic circuit" is expressly defined as a physical device including at least one hardware component configured (e.g., via operation in accordance with a predetermined configuration and/or via execution of stored machine-readable instructions) to control one or more machines and/or perform operations of one or more machines. Examples of a logic circuit include one or more processors, one or more coprocessors, one or more microprocessors, one or more controllers, one or more digital signal processors (DSPs), one or more application specific integrated circuits (ASICs), one or more field programmable gate arrays (FPGAs), one or more microcontroller units (MCUs), one or more hardware accelerators, one or more special-purpose computer chips, and one or more system-on-a-chip (SoC) devices. Some example logic circuits, such as ASICs or FPGAs, are specifically configured hardware for performing operations (e.g., one or more of the operations described herein and represented by the flowcharts of this disclosure, if such are present). Some example logic circuits are hardware that executes machine-readable instructions to perform operations (e.g., one or more of the operations described herein and represented by the flowcharts of this disclosure, if such are present). Some example logic circuits include a combination of specifically configured hardware and hardware that executes machine-readable instructions. The above description refers to various operations described herein and flowcharts that may be appended hereto to illustrate the flow of those operations. Any such flowcharts are representative of example methods disclosed herein. In some examples, the methods represented by the flowcharts implement the apparatus represented by the block diagrams. Alternative implementations of example methods disclosed herein may include additional or alternative operations. Further, operations of alternative implementations of the methods disclosed herein may combined, divided, re-arranged or omitted. In some examples, the operations described herein are implemented by machine-readable instructions (e.g., software and/or firmware) stored on a medium (e.g., a tangible machine-readable medium) for execution by one or more logic circuits (e.g., processor(s)). In some examples, the operations described herein are implemented by one or more configurations of one or more specifically designed logic circuits (e.g., ASIC(s)). In some examples, the operations described herein are implemented by a combination of specifically designed logic circuit(s) and machine-readable instructions stored on a medium (e.g., a tangible machine-readable medium) for execution by logic circuit(s).

As used herein, each of the terms "tangible machine-readable medium," "non-transitory machine-readable medium" and "machine-readable storage device" is expressly defined as a storage medium (e.g., a platter of a hard disk drive, a digital versatile disc, a compact disc, flash memory, read-only memory, random-access memory, etc.) on which machine-readable instructions (e.g., program code in the form of, for example, software and/or firmware) are stored for any suitable duration of time (e.g., permanently, for an extended period of time (e.g., while a program associated with the machine-readable instructions is executing), and/or a short period of time (e.g., while the machine-readable instructions are cached and/or during a buffering process)). Further, as used herein, each of the terms "tangible machine-readable medium," "non-transitory machine-readable medium" and "machine-readable storage device" is expressly defined to exclude propagating signals. That is, as used in any claim of this patent, none of the terms "tangible machine-readable medium," "non-transitory machine-readable medium," and "machine-readable storage device" can be read to be implemented by a propagating signal.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any way. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The claimed invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes," "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separately claimed subject matter.

The invention claimed is:

1. A system for determining a load vector on an human being, the system comprising:
   a receiver configured to:
      collect location observations related to the human being,
      filter the location observations to determine an estimated model path,
      output a set of data from the estimated model path, the set of data comprising:
         a model location,
         a model velocity,
         a model acceleration, and
         a model jerk,
      determine a load vector from the set of data, and
      scale the load vector via a scaling index; and
   a remote device configured to:
      receive the scaled load vector from the receiver, and
      display the scaled load vector for viewing by a user.

2. The method of claim 1, wherein the receiver is further configured to transmit the scaled load vector by transmitting the set of data.

3. The method of claim 1, wherein the receiver collects the location observations from one or more of a memory, an identification tag, or a database.

4. The method of claim 1, wherein the receiver is configured to determine the estimated model path using at least one of a Kalman filter, a linear regression, or a Fourier transform.

5. The method of claim 1, wherein the remote device comprises at least one of an electronic display, a mobile device, or a module.

6. The method of claim 1, wherein the receiver is configured to calculate determine the load vector from a directional load vector and a lateral load vector.

7. The method of claim 1, wherein the load vector is either a polar vector or a Cartesian vector, and wherein the Cartesian vector comprises a lateral load vector and a directional load vector with each having a magnitude and a direction.

8. A method for determining a load vector on an human being, the method comprising:
   collecting location observations related to the human being;
   filtering the location observations to determine an estimated model path;
   outputting a set of data from the estimated model path, the set of data comprising:
      a model location,
      a model velocity,
      a model acceleration, and
      a model jerk;
   determining a load vector from the set of data;
   scaling the load vector via a scaling index; and
   transmitting the scaled load vector to a remote device.

9. The method of claim 8, wherein transmitting the scaled load vector includes transmitting the set of data.

10. The method of claim 8, wherein the location observations are collected from one or more of a memory, an identification tag, or a database.

11. The method of claim 8, wherein the estimated model path is determined using at least one of a Kalman filter, a linear regression, or a Fourier transform.

12. The method of claim 8, wherein the remote device comprises at least one of an electronic display, a mobile device, or a module.

13. The method of claim 8, wherein the load vector is determined from a directional load vector and a lateral load vector.

14. The method of claim 8, wherein the load vector is either a polar vector or a Cartesian vector, and wherein the Cartesian vector comprises a lateral load vector and a directional load vector with each having a magnitude and a direction.

15. A tangible machine-readable medium comprising instructions for determining a load vector on an human being that, when executed, cause a machine to at least:
   collect location observations related to the human being;
   filter the location observations to determine an estimated model path;
   output a set of data from the estimated model path, the set of data comprising:
      a model location,
      a model velocity,
      a model acceleration, and
      a model jerk;
   determine a load vector from the set of data;
   scale the load vector via a scaling index; and
   transmit the scaled load vector to a remote device.

16. The tangible machine-readable medium of claim 15, wherein transmitting the scaled load vector further includes transmitting the set of data.

17. The tangible machine-readable medium of claim 15, wherein the location observations are collected from one or more of a memory, an identification tag, or a database, and wherein the remote device comprises at least one of an electronic display, a mobile device, or a module.

18. The tangible machine-readable medium of claim 15, wherein determining the estimated model path includes using at least one of a Kalman filter, a linear regression, or a Fourier transform.

19. The tangible machine-readable medium of claim 15, wherein the load vector is determined from a directional load vector and a lateral load vector.

20. The tangible machine-readable medium of claim 15, wherein the load vector is either a polar vector or a Cartesian vector, and wherein the Cartesian vector comprises a lateral load vector and a directional load vector with each having a magnitude and a direction.

* * * * *